United States Patent

Lee et al.

[11] Patent Number: 5,840,292
[45] Date of Patent: Nov. 24, 1998

[54] HAIR TREATMENT COMPOSITION

[75] Inventors: G. Jae Lee, Trumbull; Paul Vinski, Ridgefield, both of Conn.

[73] Assignee: Chesebrough-Pond's USA Co., Division of Conopco, Inc., Greenwich, Conn.

[21] Appl. No.: 705,070

[22] Filed: Aug. 29, 1996

Related U.S. Application Data

[63] Continuation of Ser. No. 812,529, Dec. 20, 1991, abandoned.

[51] Int. Cl.$^6$ ...................................................... A61K 7/11
[52] U.S. Cl. ................................ 424/70.16; 424/DIG. 1; 424/DIG. 2; 424/47
[58] Field of Search ............................ 424/78.08, 70.16, 424/DIG. 1, DIG. 2, 47; 525/167

[56] References Cited

U.S. PATENT DOCUMENTS

| | | | |
|---|---|---|---|
| 3,546,008 | 12/1970 | Shields et al | 117/138.8 |
| 3,734,874 | 5/1973 | Kibler et al | 260/29.2 E |
| 3,779,993 | 12/1973 | Kibler et al | 260/755 |
| 3,800,033 | 3/1974 | Flawn et al. | 424/47 |
| 3,927,199 | 12/1975 | Micchelli et al | 424/47 |
| 4,173,627 | 11/1979 | Madrange nee Dermain | 424/47 |
| 4,300,580 | 11/1981 | O'Neill et al | 132/7 |
| 4,335,220 | 6/1982 | Coney | 523/414 |
| 4,402,977 | 9/1983 | Grollier et al | 424/70 |
| 4,525,524 | 6/1985 | Tung et al | 524/601 |
| 4,772,518 | 9/1988 | Marthe | 524/430 |
| 4,859,455 | 8/1989 | Nowak, Jr. et al | 424/47 |
| 4,871,529 | 10/1989 | Sramek | 424/47 |
| 4,874,604 | 10/1989 | Sramek | 424/47 |
| 4,983,383 | 1/1991 | Maksimoski et al | 424/70 |
| 4,983,418 | 1/1991 | Murphy et al | 424/47 |
| 4,996,252 | 2/1991 | Phan et al | 524/88 |
| 5,021,238 | 6/1991 | Martino et al | 424/47 |
| 5,094,838 | 3/1992 | Benson et al | 424/47 |
| 5,158,762 | 10/1992 | Pierce | 424/47 |

FOREIGN PATENT DOCUMENTS

| | | |
|---|---|---|
| 1 222 461 | 6/1987 | Canada . |
| 2 098 624 | 11/1982 | United Kingdom . |

*Primary Examiner*—Edward J. Webman
*Attorney, Agent, or Firm*—Milton L. Honig

[57] ABSTRACT

A hair treatment composition is provided that includes a water-insoluble, dispersible polymeric resin having a viscosity of less than 2 centipoise at 25° C. when dispersed at 10% in water and a water-soluble amphoteric polymer.

6 Claims, No Drawings

HAIR TREATMENT COMPOSITION

This is a continuation application Ser. No. 07/812,529 filed Dec. 20, 1991 now abandoned.

BACKGROUND OF THE INVENTION

1. Field of the Invention

The invention relates to hairspray compositions especially formulated for use in low organic volatile systems.

2. Related Art

Hairspray compositions must meet a number of functional requirements. These include good holding ability and curl retention without giving a harsh, brittle feeling to the hair. Even under humid conditions there must be good hold and curl retention. Another requirement is that the hairspray be capable of being removed upon washing the hair at the time of shampooing. Additionally, the compositions must include the properties of low stickiness, good combing characteristics and a lack of powdering or flaking.

Various resins have been employed in hairspray compositions to achieve the aforementioned desirable properties. Among such resins are the amphoteric and anionic types.

Amphoteric resins have been extensively employed. These polymers contain cationic radicals derived from monomers such as t-butyl aminoethyl methacrylate as well as carboxyl radicals derived from monomers such as acrylic acid or methacrylic acid. Representative of this group is a product manufactured by the National Starch and Chemical Corp. under the trademark Amphomer identified on product labels by the CTFA name of Octylacrylamide/Acrylates/ Butylaminoethyl Methacrylate Copolymers. Use of Amphomer alone or in conjunction with other resins for hairsprays has been reported in U.S. Pat. Nos. 3,927,199 (Micchelli et al), 4,402,977 (Grollier et al), 4,859,455 (Nowak, Jr. et al), 4,871,529 (Sramek), 4,983,383 (Maksimoski et al), 4,983,418 (Murphy et al), 5,021,238 (Martino et al), GB 2 098 624 (Madrange) and Canadian Patent 1 222 461 (Varco).

Anionic polymeric resins have also been utilized in this art. For instance, U.S. Pat. No. 4,300,580 (O'Neill et al) discloses linear polyesters prepared from isophthalic acid, the sodium salt of 5-sulfoisophthalic acid and diethylene glycol. Eastman AQ Polymers for water-dispersed hairsprays are based on this technology. Other polyester and sulfo substituted polymer systems are described in U.S. Pat. No. 4,525,524 (Tung et al).

Environmental concerns and legislation addressing such concerns have required product reformulations to meet these challenges. Organic solvent-based sprays must, at least in part, now be substituted by water systems. Levels of organic propellants present in these water systems must also be adjusted to relatively low levels. With these constraints, certain problems have arisen. Water-dispersed systems are slow to dry. Not only do they result in wet on the hair but there is also an undesirable cool sensation that imparts a chill. Quite significantly there is also difficulty in developing a style. Resins formulated in a water-dispersed system have weak holding power.

Some systems such as the Eastman AQ Resins have good setting or holding but removability from hair is quite poor because these resins are not water soluble.

Furthermore, there is the problem of difficulties in pumpability of certain types of resins such as some amphoterics. A still further problem is that of improving glossiness to counteract resins that usually tend to dull hair.

Accordingly, it is an object of the present invention to provide a hairspray suitable for water-dispersed systems having improved holding and styling characteristics.

Another object of the present invention is to provide a hairspray composition based on a water-dispersed system that dries fairly quickly and does not impart a wet or cool feel to hair or scalp.

A further object of the present invention is to provide a hairspray composition for water-dispersed systems that improves glossiness of the hair.

A still further object of the present invention is to provide a hairspray composition for water-dispersed systems being sufficiently nonviscous for easy pumpability and to exhibit a viscosity between 3 and 7.5 centipoise at 25° C.

These and other objects of the present invention will become more evident from the following summary and detailed description.

SUMMARY OF THE INVENTION

A hair treatment composition is provided comprising:
(i) a water-insoluble, dispersible polymeric resin having a viscosity of less than about 2 centipoise at 25° C. when 10% is dispersed in water, present in an effective amount for setting hair; and
(ii) a water-soluble amphoteric polymer present in an effective amount for setting hair.

Hair treatment compositions of this invention are dispersed in water and are especially suited for delivery through nonpressurized mechanical pumps.

DETAILED DESCRIPTION

Now it has been discovered that many of the objects of the present invention can be achieved by using a hair treatment composition that includes a water-insoluble, dispersible polymeric resin having a viscosity of less than 2 centipoise at 25° C. (when dispersed at 10% in water) and a water-soluble amphoteric polymer. Each of these two components interact with the other to provide an overall superior hairspray. The water-insoluble resin provides a good to moderate hold while importantly maintaining a low viscosity, i.e. not higher than 3.0 centipoise at 25° C. On the other hand, the water-soluble amphoteric polymer provides a very substantial hold but the concentration thereof must be limited to avoid excessive thickness, i.e. above 7.5 centipoise at 25° C. The amphoteric polymer is also quite important for aiding in removing the water-insoluble resin from the hair upon shampooing.

A variety of water-insoluble dispersible polymeric resins may be employed for this invention. Most preferred are polyesters functionalized with a sulfo ($SO_3^-$) group in amounts sufficient to water-disperse the polyester. Illustrative of such resins are Eastman AQ Polymers, especially those having a glass transition temperature ranging from about 50° C. to about 70° C., preferably around 55° C. Most preferred is Eastman AQ 55S which is a polyester identified as an ethylene diglycol/cyclohexanedimehtanol/ isophthalates/sulfoisophthalates resin. These polyesters can be derived through esterification of:
(a) at least one dicarboxylic acid;
(b) at least one diol, at least 20 mole percent of this diol component being a poly (ethylene glycol) having a formula H—(—OCH$_2$CH$_2$)$_n$OH wherein n is an integer from 2 to about 10, and
(c) at least one difunctional monomer containing a SO$_3$M group attached to an aromatic nucleus, wherein M is hydrogen or a metal ion such as sodium, lithium or potassium.

Preferably the sulfo-monomer component constitutes at least from about 8 to 45 mole percent of the sum of the moles of components (a) and (c), the acid components and the diol being substantially equimolar.

Amounts of the water-insoluble dispersible polymeric resin will range from about 0.5 to about 10%, preferably from about 1.5 to about 8%, optimally between about 2 and about 6% by weight.

The second component of the present invention is a water-soluble amphoteric polymer. Advantageously, this polymer is an acrylate copolymer, especially an octylacrylamide/acrylates/butylaminoethyl methacrylate copolymer. Such material is available from the National Starch and Chemical Company under the trademark Amphomer® LV-71. The acrylate-based copolymers are generally defined as containing from 40 to 60% of a $C_3$–$C_{12}$, preferably $C_3$–$C_8$, alkyl methacrylate, 20 to 40% of a $C_4$–$C_{10}$ N-substituted alkyl acrylamide, and 10 to 25%, preferably 19 to 25% acrylic acid or methacrylic acid, wherein the percentages total 100%. More preferably, these copolymers comprise 45–55% isobutylmethacrylate, 25 to 35% N-t-octyl acrylamide, and 19 to 25% acrylic acid.

Amounts of the water-soluble amphoteric polymer resin may range from about 0.5 to about 10%, preferably from about 1.5 to about 5%, optimally between about 2 and about 4% by weight.

Compositions of the present invention will also include water as a solvent carrier for the resins and other components. Water will be present in amounts ranging from about 10% to about 99%, preferably from about 40% to about 95% by weight.

With certain of the resins it may be necessary to neutralize some acidic groups to promote solubility/dispersibility. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). Amounts of the neutralizing agents will range from about 0.001 to about 10% by weight.

The present hairspray compositions may be formulated in aerosol or nonaerosol forms. However, the compositions are particularly useful in nonaerosol form to be delivered by a mechanical pumpspray.

Small quantities of surfactant ranging anywhere from 0.1 to about 10%, preferably from about 0.1 to about 1%, optimally about 0.3% by weight may be present in the compositions of the invention. The surfactant may be an anionic, nonionic or cationic emulsifier. Particularly preferred are nonionic emulsifiers which are formed from alkoxylation of hydrophobes such as fatty alcohols, fatty acids and phenols. Illustrative of such material is Triton X-100, and isooctyl phenyl polyethoxy-ethanol.

Resins when deposited upon hair quite often impart dullness. Counteraction of the dullness effect may be achieved by incorporating low levels of $C_1$–$C_{20}$ fatty alcohol esters. Particularly preferred is cetearyl octanoate. Amounts of these luster imparting agents will range from about 0.001 to about 1%, preferably from about 0.01 to about 0.5%, optimally from about 0.02 to about 0.1% by weight.

Compositions of this invention may contain any other ingredient normally used in hairsprays. These other ingredients may include antifoam agents, proteins, antioxidants, fragrances, antimicrobials and sunscreens. Each of these ingredients will be present in an amount effective to accomplish its purpose.

The following examples will more fully illustrate the embodiments of this invention. All parts, percentages and proportions referred to herein and the appended claims are by weight unless otherwise indicated.

EXAMPLE 1

Hairspray composition typical of the present invention is outlined below.

| Component | Weight Percent |
| --- | --- |
| Water | 92.975 |
| Amphomer LV-71 | 3.300 |
| Eastman AQ 55 | 2.200 |
| AMP-95 | 0.693 |
| Triton X-100 | 0.300 |
| Methylparaben | 0.200 |
| Fragrance | 0.150 |
| Dow Corning 190 SU | 0.100 |
| DMDM Hydantoin | 0.050 |
| DL-panthenol | 0.001 |
| Vitamin E Acetate | 0.001 |

EXAMPLE 2

A series of experiments were conducted to evaluate the most effective relative concentrations of the Eastman AQ 55S resin to the Amphomer LV-71 polymer. These experiments utilized the following test procedure.

Film "hardness," a measure of hair hold capability, was evaluated by evenly applying 2–4 grams of concentrate onto an 8"×8" glass plate. Samples were allowed to dry overnight to achieve a thick, dry film. Observations of gelling of the film were recorded. Using a sharp-pointed tool, the film was lightly "scratched" upon the glass plate. Observations were then recorded with regard to hardness and brittleness. A ranking was performed in comparison with known controls.

The above test was performed on the composition of Example 1 except for the stated variations in resin and polymer. Table I outlines spray characteristics and hair hold capability as a function of resin to polymer ratios.

TABLE I

| Composition | Ratio of AQ 55S:Amphomer | Spray Characteristics | Hair Hold Capability |
| --- | --- | --- | --- |
| I-A | 100:0 | Too misty; Uncontrollable | ↑ Poor hold |
| I-B | 80:20 | ↑ Acceptable range | ↑ Acceptable range |
| I-C | 60:40 | \| | \| |
| I-D | 40:60 | \| | \| |
| I-E | 20:80 | ↓ | \| |
| I-F | 0:100 | Too coarse to spray; clogs valve and and spits | ↓ Better hold |

Composition I-D having a ratio of AQ resin to Amphomer of 40:60 exhibited the optimum performance in spray characteristics and hair hold capability. The acceptable range for spray characteristics was from 80:20 to 20:80 ratio of the respective resin and polymer.

The foregoing description and Examples illustrate selected embodiments of the present invention. In light thereof, various modifications will be suggested to one skilled in the art, all of which are within the spirit and purview of this invention.

What is claimed is:

1. A hair treatment composition comprising:
   (i) a water-insoluble, dispersible polymeric resin having a viscosity of less than about 2 centipoise at 25° C. when 10% is dispersed in water, present in an effective amount for setting hair, said resin being a diglycol/cyclohexanedimethanol/isophthalates/sulfoisophthalates polyester; and
   (ii) a water-soluble amphoteric polymer present in an effective amount for setting hair, said amphoteric polymer being an acrylamide/acrylate/butylaminoethyl methacrylate copolymer, wherein said water-insoluble resin and amphoteric polymer have a relative wt. % ratio of 3:2 to 1:4.

2. A composition according to claim 1 further comprising a $C_{10}$–$C_{20}$ fatty acid ester present in an effective amount to provide luster to hair.

3. A composition according to claim 2 wherein said ester is cetearyl octanoate present in an amount from about 0.001 to about 0.5% by weight.

4. A composition according to claim 1 wherein water is present in an amount from about 10 to about 99% by weight.

5. A composition according to claim 1 wherein the water-insoluble resin and amphoteric polymer have a relative wt. % ratio of 3:2 to 2:3.

6. A composition according to claim 1 wherein the water-insoluble resin and amphoteric polymer have a relative wt. % ratio of about 2:3.

* * * * *